(12) United States Patent  (10) Patent No.: US 9,097,700 B2
Brown et al.  (45) Date of Patent: Aug. 4, 2015

(54) GLUCOSE MEASUREMENT SYSTEM WITH HIGH-CAPACITY CARTRIDGE AND CAPABILITY OF MORE FREQUENT REPLENISHMENT

(71) Applicant: Bayer HealthCare LLC, Tarrytown, NY (US)

(72) Inventors: Daniel Brown, Edwardsburg, MI (US); Martin Antoine Mathelier, Garnerville, NY (US); Sung-Kwon Jung, Granger, IN (US)

(73) Assignee: Bayer HealthCare LLC, Whippany, NJ (US)

( * ) Notice: Subject to any disclaimer, the term of this patent is extended or adjusted under 35 U.S.C. 154(b) by 83 days.

(21) Appl. No.: 13/729,765

(22) Filed: Dec. 28, 2012

(65) Prior Publication Data

US 2013/0168403 A1    Jul. 4, 2013

Related U.S. Application Data

(60) Provisional application No. 61/581,162, filed on Dec. 29, 2011.

(51) Int. Cl.
  *G01N 33/487*   (2006.01)
  *B65B 5/08*   (2006.01)

(52) U.S. Cl.
  CPC ............ *G01N 33/48778* (2013.01); *B65B 5/08* (2013.01)

(58) Field of Classification Search
  USPC ........ 221/30, 31, 34, 36, 41, 69, 87, 154, 279
  See application file for complete search history.

(56) References Cited

U.S. PATENT DOCUMENTS

| 4,217,331 | A | * | 8/1980 | Schaub | 422/265 |
|---|---|---|---|---|---|
| 5,510,266 | A | * | 4/1996 | Bonner et al. | 436/43 |
| 5,632,410 | A | * | 5/1997 | Moulton et al. | 221/79 |
| 5,645,798 | A | * | 7/1997 | Schreiber et al. | 422/410 |
| 5,660,791 | A | | 8/1997 | Brenneman et al. | |
| 5,720,924 | A | * | 2/1998 | Eikmeier et al. | 422/550 |
| 5,863,800 | A | * | 1/1999 | Eikmeier et al. | 436/48 |
| 6,428,664 | B1 | * | 8/2002 | Bhullar et al. | 204/403.03 |
| 6,497,845 | B1 | | 12/2002 | Sacherer | |
| 6,534,017 | B1 | | 3/2003 | Bottwein et al. | |

(Continued)

FOREIGN PATENT DOCUMENTS

| EP | 1321769 A1 | 6/2003 |
|---|---|---|
| EP | 1726950 A1 | 11/2006 |

(Continued)

*Primary Examiner* — Gene Crawford
*Assistant Examiner* — Kelvin L Randall, Jr.
(74) *Attorney, Agent, or Firm* — Lerner, David, Littenberg, Krumholz & Mentlik, LLP

(57) ABSTRACT

The present disclosure relates to packaging containers for holding a plurality of test sensors. The packaging container may include a first semi-circular housing and a second semi-circular housing. The first semi-circular housing has a plurality of first test sensor containing regions. Each of the plurality of the first test sensor containing regions is adapted to contain at least one test sensor having a top portion covered by a foil cover. The second semi-circular housing has a plurality of second test sensor containing regions. Each of the plurality of the second test sensor containing regions is adapted to contain at least one test sensor. The second semi-circular housing has a top portion. The first semi-circular housing and the second semi-circular housing are positioned adjacent to each other.

17 Claims, 8 Drawing Sheets

(56) References Cited

U.S. PATENT DOCUMENTS

| | | |
|---|---|---|
| 6,827,899 B2 | 12/2004 | Maisey et al. |
| 6,988,996 B2 | 1/2006 | Roe et al. |
| 6,997,343 B2 | 2/2006 | May et al. |
| 7,138,089 B2 | 11/2006 | Aitken et al. |
| 7,211,096 B2 * | 5/2007 | Kuhr et al .................... 606/182 |
| 7,264,139 B2 | 9/2007 | Brickwood et al. |
| 7,270,247 B2 | 9/2007 | Charlton |
| 7,364,699 B2 | 4/2008 | Charlton |
| 7,604,592 B2 * | 10/2009 | Freeman et al. ............. 600/309 |
| 7,790,106 B2 * | 9/2010 | Uchigaki et al. ............... 422/63 |
| 7,913,838 B2 * | 3/2011 | Zhong ........................... 206/305 |
| 8,158,078 B2 * | 4/2012 | Chan et al. .................... 422/401 |
| 8,296,918 B2 * | 10/2012 | Alden et al. ................. 29/407.01 |
| 8,372,016 B2 * | 2/2013 | Freeman et al. ............. 600/583 |
| 8,574,510 B2 | 11/2013 | Gofman et al. |
| 2002/0057993 A1 | 5/2002 | Maisey et al. |
| 2002/0076349 A1 | 6/2002 | Aitken et al. |
| 2003/0223906 A1 | 12/2003 | McAllister et al. |
| 2007/0119710 A1 * | 5/2007 | Goldberger et al. ..... 204/403.01 |
| 2008/0093235 A1 | 4/2008 | Zhong et al. |
| 2008/0094804 A1 | 4/2008 | Reynolds et al. |
| 2008/0118399 A1 | 5/2008 | Fleming |
| 2008/0164164 A1 * | 7/2008 | Zhong ........................... 206/305 |
| 2008/0164280 A1 | 7/2008 | Kuriger et al. |
| 2008/0181818 A1 | 7/2008 | Ruan |
| 2008/0190766 A1 | 8/2008 | Rush et al. |

FOREIGN PATENT DOCUMENTS

| | | |
|---|---|---|
| EP | 1726951 A1 | 11/2006 |
| WO | 0123885 A1 | 4/2001 |
| WO | 0208753 A2 | 1/2002 |
| WO | 0218940 A2 | 3/2002 |
| WO | 03042691 A1 | 5/2003 |
| WO | 2004063747 A1 | 7/2004 |
| WO | 2006002432 A1 | 1/2006 |
| WO | 2006019665 A1 | 2/2006 |
| WO | 2006044850 A1 | 4/2006 |
| WO | 2006065754 A2 | 6/2006 |
| WO | 2006076721 A2 | 7/2006 |
| WO | 2007085438 A2 | 8/2007 |
| WO | 2007147494 A2 | 12/2007 |
| WO | 2008111937 A1 | 9/2008 |

* cited by examiner

GLUCOSE MEASUREMENT SYSTEM WITH HIGH-CAPACITY CARTRIDGE AND CAPABILITY OF MORE FREQUENT REPLENISHMENT

CROSS-REFERENCE TO RELATED APPLICATIONS

The present application claims the benefit of the filing date of U.S. Provisional Patent Application No. 61/581,162 filed Dec. 29, 2011, the disclosure of which is hereby incorporated herein by reference.

BACKGROUND OF THE INVENTION

The present disclosure generally relates to a packing container for test sensors and, more particularly, to a circular packing container for test sensors to be used in conjunction with a liquid sample monitoring device to determine an analyte concentration in a liquid sample.

Monitoring systems are used for determining the presence or concentration of analytes in body fluids, such as glucose, cholesterol, alcohol, and hemoglobin in blood, interstitial fluid, or chemical substances in saliva. These monitoring systems require frequent use of test sensors. The test sensors may be provided individually, but most find it convenient to utilize a cartridge of strips.

Certain self-monitoring systems are portable, handheld testing devices. The portable nature of these devices enables a user to conveniently test their blood glucose levels wherever the users may be. These testing devices typically include, or at least are able to hold, test sensors or strips for testing harvested blood or any other suitable liquid sample. The test sensors may include a reaction area containing a reagent for producing a measurable reaction with an analyte indicative of the presence or concentration of said analyte. For example, some reagents may produce a measureable reaction with glucose indicative of the blood glucose concentration level.

Patients suffering from various forms of diabetes or any condition resulting in abnormal blood glucose concentration levels often need to test their blood to determine whether any corrective action needs to be taken. For example, a patient that has detected an irregularly high blood glucose concentration level may use insulin to lower his or her blood glucose concentration. Failure to take the appropriate corrective action may result in serious adverse health effects on the individual. Given the importance of monitoring blood glucose concentration levels, engineers and scientists have developed self-monitoring systems with sensors adapted to test a blood sample.

Conventional test sensors can only be used once per test. As a consequence, users of portable, handheld self-monitoring devices often carry a cartridge or container holding a plurality of test sensors. Examples of cartridges designed for holding test sensors are described in U.S. Pat. No. 5,660,791 and U.S. Patent Application Publication Nos. 2008/0093235 and 2008/0164164, the entire disclosures of each of which are hereby incorporated by reference. Conventional cartridges or containers, however, may be bulky and difficult to carry. Since users typically need to replenish their portable self-monitoring devices often, there is a need for improving and decreasing the size of the cartridges and containers designed for holding test sensors. There is a particular need for a replenishment system that allows for replenishment of less than all of the test sensors of a given cartridge or holder.

BRIEF SUMMARY OF THE INVENTION

The present disclosure relates to test sensor packaging assemblies for use with a liquid sample monitoring device. The packaging assembly is designed to hold and individually seal a plurality of test sensors or strips. These test sensors contain a reagent capable of producing a measurable reaction with an analyte indicative of the presence or concentration of said analyte. The test sensors may be used in conjunction with a liquid sample meter to make a quantitative analysis of the analytes in the liquid sample. Preferably, the packaging assembly includes a plurality of housings holding the test sensors. In this manner, one of the plurality of housings may be replaced upon exhaustion without the need of replacing the entire packaging assembly. Typically, the housings will complete at least a portion of a circle.

In one embodiment of the present disclosure, the packaging assembly, which includes a first semi-circular housing and a second semi-circular housing positioned adjacent to each other, can hold a plurality of test sensors. Each of the first and second semi-circular housings has a plurality of test sensor containing regions. Each test sensor containing region is dimensioned and adapted to hold at least one test sensor. The first semi-circular housing has a top portion covered by a foil cover. The second semi-circular housing has a top portion. The outer wall of the first semi-circular housing may extend in a non-perpendicular manner from the top portion. The first semi-circular housing may be removed from said packaging container and replaced with a third semi-circular housing having a plurality of third test sensor containing regions, each of the plurality of third test sensor containing regions being adapted to contain at least one test sensor. During operation, breaking one foil cover only opens individual test sensor containing regions. The first semi-circular housing and the second semi-circular housing may combine to form a circular cartridge.

In another embodiment, the packaging container includes at least two housings forming a circle. Each housing has at least one test sensor containing region adapted to contain at least one test sensor. The housings have top portions and bottom portions that are substantially parallel with respect to each other. Each top portion of the housings is covered by a foil cover. The packaging container further includes a guiding system for guiding the ejection of each test sensor from each test sensor containing region. The guiding system includes a guide member associated with each test sensor and a slot defined along an outer wall of each test sensor containing region. The slot is dimensioned to receive the guide member and the test sensor. The guide member has a shape that allows the test sensor to turn about degrees when ejected from the test sensor containing region. The guide member may have a partial spiral shape. The packaging container may only have two housings. The outer wall of each test sensor containing region may be tapered with respect to the top portions and bottom portions of the housing. The guiding system may be adapted to cut the foil cover.

The present disclosure further relates to methods for replacing a housing of the packaging container. In one embodiment, the method includes providing a packaging container including at least two housings. Each housing has at least one test sensor containing region adapted to contain at least one test sensor. The method further includes replacing one housing of the at least two housings with another housing while the remaining housings remain in the packaging container.

The present disclosure further discloses another embodiment of a packaging container for holding a plurality of test sensors. This embodiment includes at least two housings forming a circle. Each housing has at least one test sensor containing region covered by a foil cover. Each test sensor containing region is adapted to contain at least one test sensor and has a guiding mechanism for turning the at least one test sensor about 90 degrees upon ejection from one of the at least two housings. The guiding mechanism includes a hollow compartment in an outer region of each test sensor containing region. The hollow compartment includes a first inclined wall and a second inclined wall. The first inclined wall is oriented at an acute angle relative to the second inclined wall so that the at least one test sensor turns about 90 degrees upon passing through the hollow compartment.

The present disclosure further discloses another embodiment of a packaging container for holding a plurality of test sensors includes first and second semi-circular housings adjacent one another. The first semi-circular housing has a plurality of first test sensor containing regions and each of the plurality of the first test sensor containing regions is adapted to contain at least one test sensor. The second semi-circular housing also has a plurality of second test sensor containing regions and each of the plurality of the second test sensor containing regions is adapted to contain at least one test sensor. The second semi-circular housing has a top portion. The first semi-circular housing and the second semicircular housing combine to form a circular cartridge.

An alternative embodiment includes the first semi-circular housing having an outer wall that extends in a non-perpendicular direction away from said top portion. Each of the plurality of first test sensor containing regions may also further comprise an opening and the at least one test sensor in each of the plurality is capable of being ejected through the opening. The plurality of first test sensor containing regions may further comprise a foil cover and a cutting assembly for removing the foil cover each time one of the first test sensors is to be ejected through the opening of the respective test sensor containing region. The cutting assembly may further include a base and a cutting edge that extends from the base. Movement of the base causes movement of the cutting edge and a rod that engages the cutting assembly. The test strip may further comprise a slot constructed and arranged to receive the rod and movement of the cutting assembly may cause movement of the test strip.

In an alternative embodiment, the plurality of test sensor containing regions may alternatively have a top portion covered by a foil and each time a test sensor is ejected from the test sensor containing region, at least a portion of the foil covering the individual test sensor containing region from which the test sensor is ejected is cut and the foil covering the remaining individual test sensor containing regions is not cut. This allows for the remaining test strips in the remaining plurality of test sensor containing regions to remain intact and unexposed until a user desires to conduct a test and use a test strip.

In another embodiment, the first semi-circular housing may be removed from the packaging container and replaced with a third semi-circular housing having a plurality of third test sensor containing regions. The first semi-circular housing may be replaced with the third semi-circular housing while the second semi-circular housing is still in place. Each of the plurality of the third test sensor containing regions may be adapted to contain at least one test sensor.

The present disclosure further discloses another embodiment of a packaging container for holding a plurality of test sensors. The packaging container includes at least two housings forming at least a portion of a circle, test sensor containing regions, and a guiding system. Each of the at least two housings have at least one test sensor containing region. The test sensor containing regions are adapted to contain at least one test sensor. The housings may have top portions and bottom portions that are substantially parallel with respect to each other and each top portion may be covered by a foil cover. The guiding system may guide the ejection of each test sensor from each test sensor containing region. The guiding system may include a guide member associated with each test sensor and a slot defined along an outer wall of each test sensor containing region, the slot being dimensioned to receive the guide member and the test sensor, the guide member having a shape that allows the test sensor to rotate from a first position to a second position when ejected from the test sensor containing region. The guide member may alternatively have a partial spiral shape and may also be adapted to cut the foil cover. Additionally, the outer wall may be tapered with respect to the top portions and bottom portions of said housing.

In alternative embodiments, the test sensor may rotate about 90 degrees when moving from the first position to the second position. The at least two housings may further comprise opposed sidewalls extending between the top and bottom portions. When the at least one test sensor in each of the two housings is in the first position, each of the at least one test sensors has a major surface parallel to the opposed side walls and a minor surfaces parallel to the top portion. When the test sensor is moved into the second position, the major surface of the test sensor is parallel to the top portion and the minor surface is parallel to the opposed sidewalls.

In another alternative embodiment, the housings further comprise opposed sidewalls extending between the top and bottom surfaces. When the test sensor is in the first position, the test sensor has a minor surface parallel to the opposed side walls and major surfaces parallel to the top surface. When the test sensor is in the second position, the minor surface of the test sensor is parallel to the top surface and the major surface is parallel to the sidewalls.

In yet another alternative embodiment, the at least two housings includes only two housings. There may also be a cutting assembly for cutting the foil cover. The cutting assembly may comprise a base and a cutting edge extending from the base, wherein movement of the base causes movement of the cutting edge across the foil cover.

BRIEF DESCRIPTION OF THE DRAWINGS

Various embodiments of the present invention will now be described with reference to the appended drawings. It is appreciated that these drawings depict only some embodiments of the invention and are therefore not to be considered limiting in its scope.

DETAILED DESCRIPTION

Figure 1:
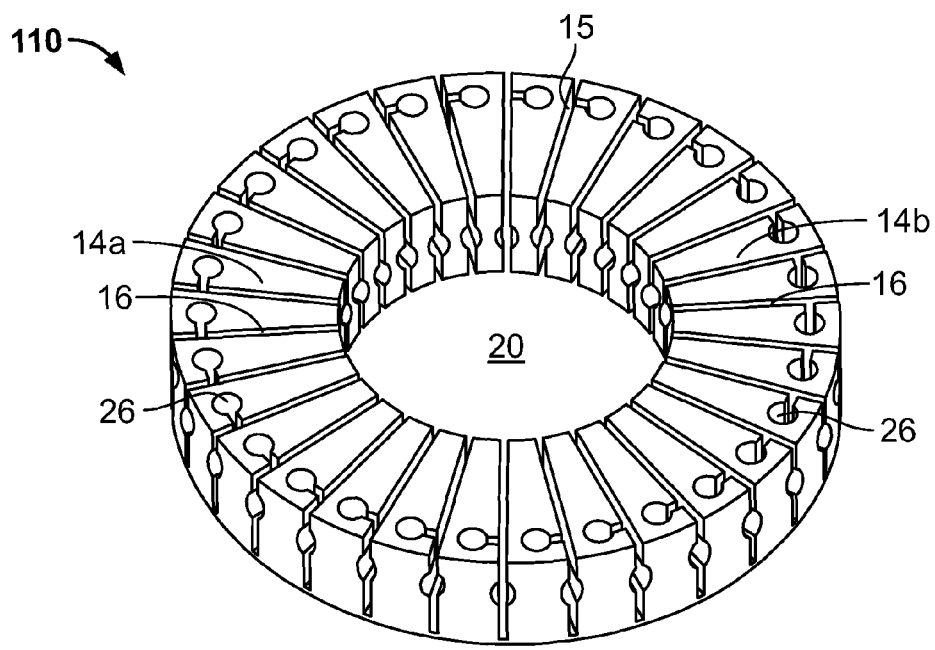
FIG. 1 is a perspective view of a test sensor packaging assembly including two segments.
Figure 2:
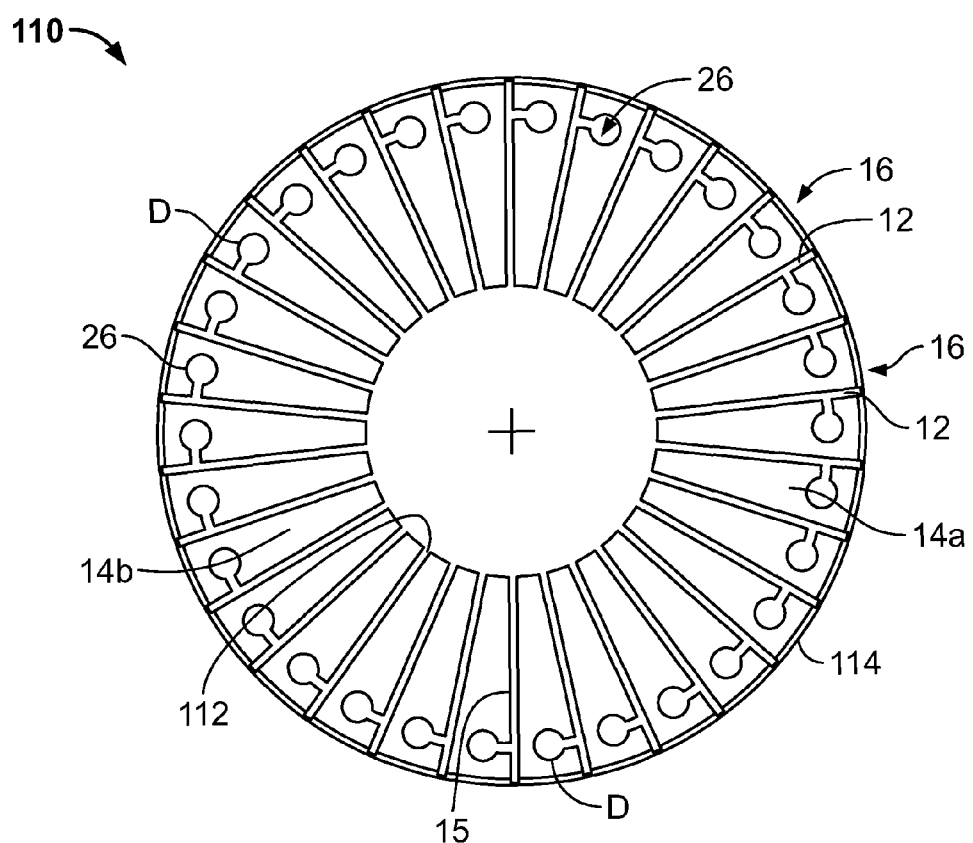
FIG. 2 is a top view of the test sensor packaging assembly of FIG. 1.

FIGS. 1 and 2 show an embodiment of a test sensor packaging assembly 110 for holding a plurality of test sensors adapted for determining a user's analyte concentration level in a fluid sample. Although the following discussion describes the use of test sensors for determining the glucose concentration in blood, the presently disclosed test sensor packaging assembly 110 may contain test sensors designed to determine the concentration of other analytes in other types of samples. For example, test sensor 12 may alternatively measure glucose, lipid profiles (e.g., cholesterol, triglycerides, low-density lipoprotein (LDL) and high-density lipoprotein (HDL)), microalbumin, hemoglobin $A_{1C}$, fructose, lactate, bilirubin, or other analytes). The analytes may be in, for example, a whole blood sample, a blood serum sample, a blood plasma sample, or body fluids like interstitial fluid (ISF) and urine.

Test sensor packaging assembly 110 includes at least two housing segments 14a, 14b forming a complete circle. While the drawings show housing segments 14a, 14b forming a complete circle, housing segments 14a, 14b may alternatively form other shapes, such as partly-circular, polynomial, rectangular, elliptical, oval, or any other suitable shape. Housing segments 14a, 14b may be made of a polymeric material in order to increase the structural integrity of the test sensor packaging assembly 110. While the drawings show only two housing segments 14a, 14b, test sensor packaging assembly 110 may include more than two housing segments 14a, 14b. As shown in FIG. 1, each of the housing segments 14a, 14b may have a semi-circular shape. In this embodiment, the two housing segments 14a,14b may be two semi-circular portions (or two halves) that when joined together form a complete circle. In the case of greater than two housing segments, the shape may be arced or curved. Collectively, the housing segments 14a, 14b may form a circular shape, leaving an internal cavity 20 within their collective boundary. Alternatively, the housing segments 14a, 14b (or more) may form an incomplete circle or an arc. In some embodiments, the housing segments 14a, 14b (or more) may collectively have a linear or rectangular configuration. Test sensor packing assembly 110 may also have other suitable shapes, such as square, rectangular, or oval.

Each housing segment 14a, 14b can hold a plurality of test sensors 12 (FIG. 2). In certain embodiments, each housing segment 14a, 14b may hold between 15 and 25 test sensors 12. In one specific embodiment, housing segments 14a, 14b can collectively hold 30 test sensors 12, preferably split equally between the two segments.

The segmented test sensor packaging assembly 110 may enhance the user's experience. Typically, large-capacity conventional test sensor packaging containers can hold less than a single-day's supply of sensors, particularly where some of the capacity has been previously exhausted. Accordingly, the user of these conventional containers must carry around a full cartridge for the impending need to replenish the onboard sensory inventory. By segmenting the test sensor packaging assembly 110, the user can replenish the analyte measuring system in some increments, thereby obviating the need of carrying around a complete spare on his or her person.

Segmenting the test sensor packaging assembly 110 also facilitates its manufacturing process. For instance, the internal cavity 20 of the test sensor packaging assembly 110 may be more accessible to machinery during the manufacturing process than in conventional circular cartridges where the internal cavity forms a portion of the cartridge.

As discussed above, test sensor packaging assembly 110 includes two or more housing segments (14a or 14b). Each housing segment 14a, 14b has a plurality of test sensor containing regions 16. In some embodiments, each housing segment 14a, 14b may have between 15 to 25 sensor containing regions 16 dimensioned to receive a test sensor 12. In one embodiment, test sensor packaging assembly 110 includes 30 test sensor containing regions 16. Each test sensor containing region 16 is dimensioned and configured to hold one or more test sensors 12, typically in a sideways orientation, such that sides of the test sensor 12 are oriented toward the top portion 116 and bottom portion 118 of the housing segments 14a, 14b. While the test sensor containing regions 16 shown in the figures are adapted to hold only a single test sensor 12, the test sensor container regions 16 may hold more than one test sensor 12. The test sensor containing regions 16 may each have a slot or slit 15 extending between an inner periphery or diameter 112 and an outer periphery or diameter 114 of the test sensor packaging assembly 110. Slot 15 is dimensioned to receive at least one test sensor 12 to eject the test sensor 12 from the housing segment 14a or 14b.

As seen in FIGS. 1 and 2, each housing segment 14a, 14b may include desiccant cavities 26 in fluid communication with each of the corresponding test sensor containing regions 16. Desiccant material "D" is disposed in the desiccant cavities 26 to maintain an appropriate humidity level in the test sensor containing regions 16, thereby avoiding potentially adverse effects on the reagent material in the test sensors 12. In certain embodiments, each desiccant cavity 26 may be in fluid communication with only a single test sensor containing region 16. Consequently, a test sensor containing region 16 can be maintained at the appropriate humidity level, even when another test sensor containing region 16 is opened. For example, the opening of one test sensor containing region 16 of a housing segment 14a or 14b may not affect another test sensor containing region 16. The desiccant material "D" may be in the form of a bead. Alternatively or additionally, housing segments 14a, 14b may be made or molded from a desiccant-containing resin. As discussed below with regard to FIG. 4, a plurality of foil covers 124 are secured over the housing segments 14a, 14b to seal each test sensor containing region 16. Each foil cover 124 may seal a corresponding housing segment 14a, 14b. Accordingly, the number of foil covers 124 may correspond to the number of housing segments. In particular, foil covers 124 seal the top and/or bottom portions 116, 118 of the housing segments 14a, 14b, as well as the outer periphery 114. Each housing segment 14a, 14b may be covered by more than one foil cover 124.

Figure 3:
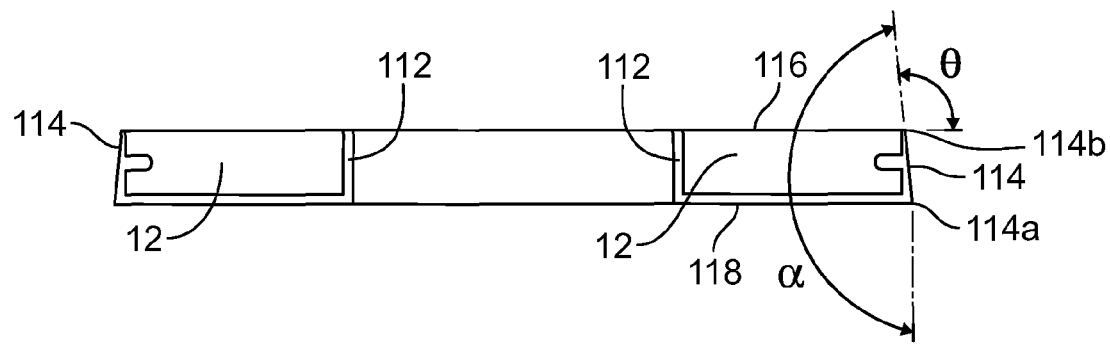
FIG. 3 is a side cross-sectional view of the test sensor packaging assembly of FIG. 1.

With reference to FIG. 3, test sensor packaging assembly 110 may include an outer periphery 114 defining an oblique angle θ relative to its top portion 116 and bottom portion 118. Angle θ may range between 4 and 8 degrees. In some embodiments, angle θ may be about 6 degrees. Outer periphery 114 also defines an angle α between its first end 114a adjacent to the bottom portion 118 and its second end 114b adjacent to the top portion 116. Angle α may range between 170 and 178 degrees. In certain embodiments, angle α may be about 174 degrees. The angled outer periphery 114 of the test sensor packaging assembly 110 obviates the need for a cutting edge on the test sensor 12. As discussed in detail below, foil cover 124 is cut at two locations when a test sensor or strip 12 is ejected from the test sensor containing region 16. During ejection, a blade or knife 166 severs a portion of foil cover 124 located along the slit 15 of each test sensor containing region 16, and the test sensor 12 punctures the portion of the foil cover 124 covering the outer periphery 114 of the housing segment 14a or 14b. Conventional test sensors or strips 12 usually have an angled leading face to facilitate piercing the portion of the foil cover 124 covering the outer periphery 114 of the housing segments 14a, 14b during ejection. In one of the presently disclosed embodiments, however, the outer periphery 114 of the housing segments 14a, 14b is angled relative to top or bottom portions 116, 118 to facilitate puncturing the foil cover 124 with the ejecting test sensor 12. In such embodiment, the test sensor 12 does not necessarily have an angled leading face.

Figure 4:
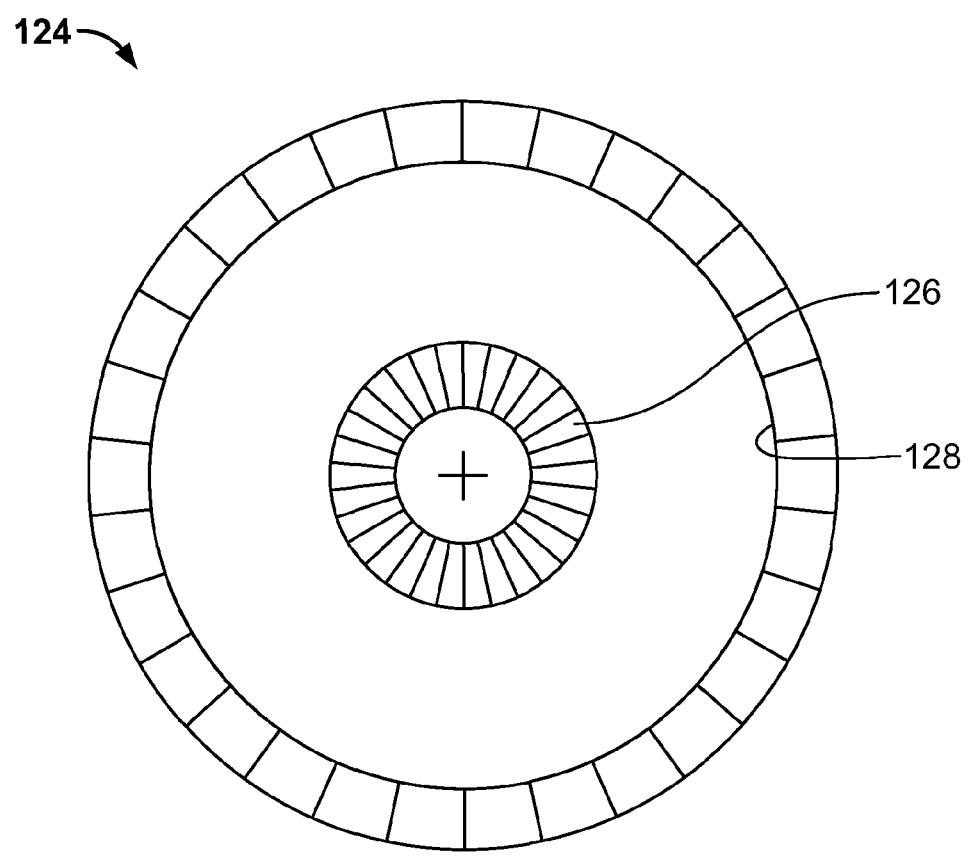
FIG. 4 is a top view of a sealing component of the test sensor packaging assembly of FIG. 1.

FIG. 4 illustrates a foil cover or sealing component 124 configured and dimensioned to cover at least the top portion 116 and outer periphery 114 of the test sensor packaging assembly 110. Foil cover 124 may also be dimensioned to cover the inner periphery 112 of the test sensor packaging assembly 110. When foil cover 124 is placed over the top portion 116 of the test sensor packaging assembly 110, it seals the test sensors 12 within the test sensor containing regions 16. In the embodiment depicted in FIG. 4, foil cover 124 includes an inner folding line 126 and an outer folding line 128. The inner folding line 126 and the outer folding line 128 may have circular shapes, or shapes matching the test sensor packaging assembly 110. During assembly, foil cover 124 may be folded along the folding lines to ensure that it covers at least a portion of the inner periphery 112 and the outer periphery 114 of the test sensor packaging assembly 110. Foil cover 124 may be secured to the housing segments 14a, 14b by any suitable means. For example, foil cover 124 can be heat-welded or glued to the housing segments 14a or 14b.

Figure 5A:
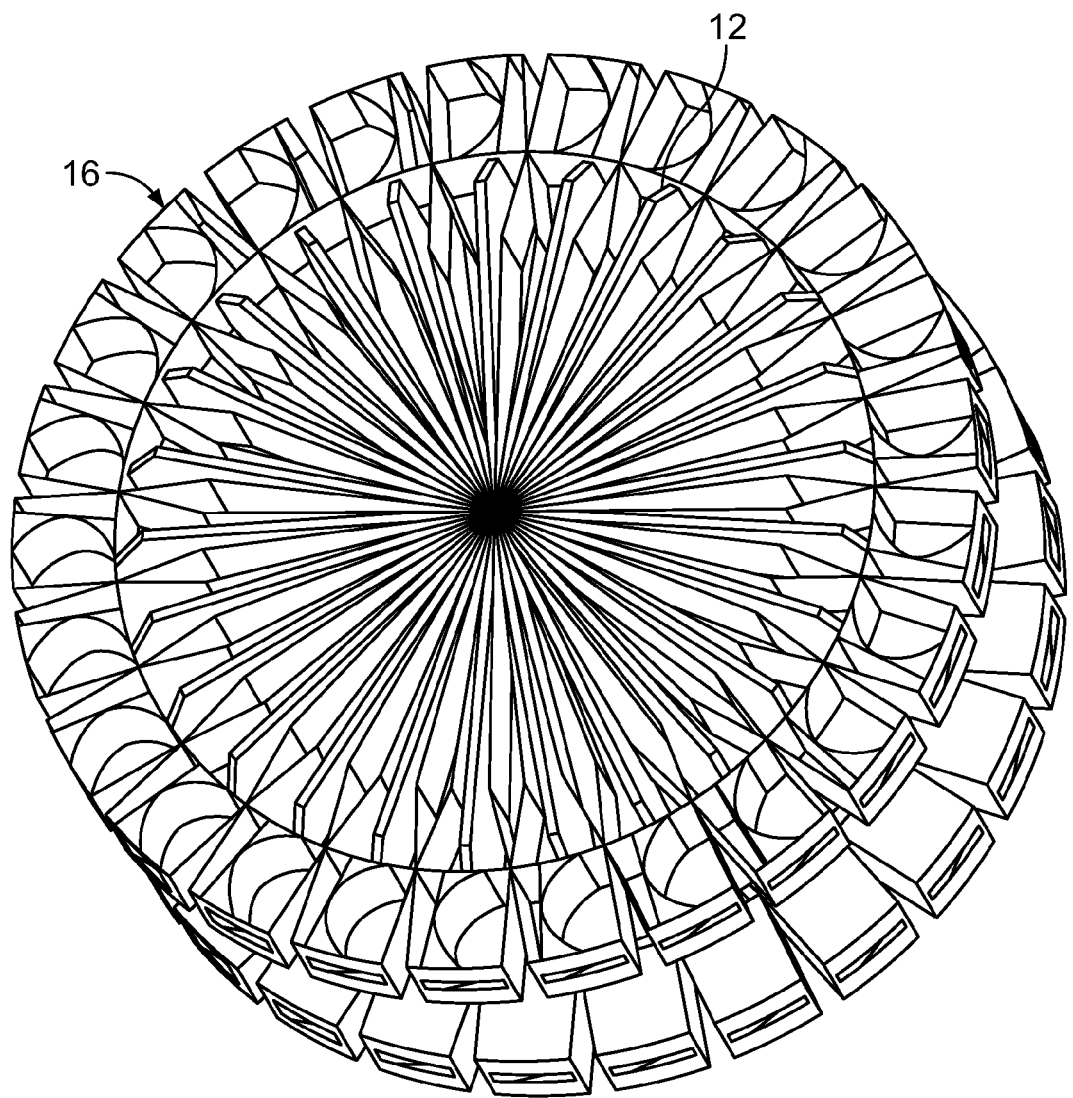
FIG. 5A is a perspective view of an array of test sensor container regions of the test sensor packaging assembly of FIG. 1.
Figure 5B:
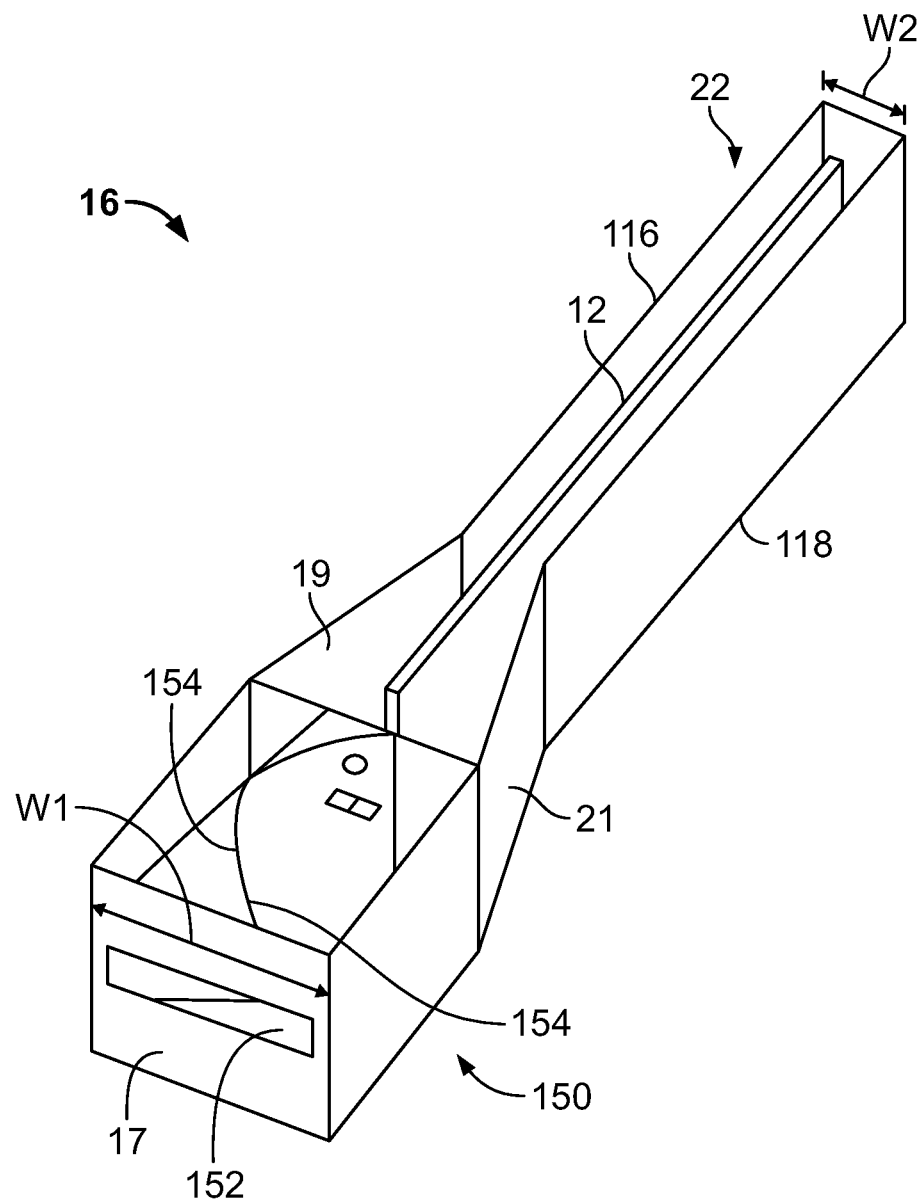
FIG. 5B is an enlarged perspective view of a single test sensor container region of FIG. 5A.

FIG. 5A depicts an array of test sensor containing regions 16, while FIG. 5B shows a single test sensor containing region 16. Test sensor packaging assembly 110 includes a guiding mechanism 150 for each test sensor containing region 16. Guiding mechanism 150 can guide the movement of the test sensor 12 relative to the test sensor containing region 16. As seen in FIG. 5B, guiding mechanism 150 includes a slot 152 positioned on an outer surface 17 of the test sensor containing region 16 and a guide member 154 associated with the test sensor 12. Guide member 154 is dimensioned to slidably pass through slot 152. As discussed in detail below, guide member 154 has a particular shape (e.g., partial spiral) to guide the ejection of the test sensor 12 from test sensor containing region 16, causing the test sensor 12 to turn or rotate about 90 degrees when ejected from the test sensor containing region 16. In this regard, a test sensor 12 is stored in the housing segment 14a or 14b in an upright position with its sides or the minor surfaces of the test sensor 12 facing toward the top and bottom portions 116, 118, respectively, and the major surface of the test sensor (or the testing surface) facing the respective sidewalls 19,21. This allows for the test sensor 12 to be presented to a user in a rotated orientation such that it is oriented for use in its typical flat orientation. It is to be appreciated that in alternative embodiments, the guide member 154 can also take on alternative configurations if it is desired to orient the test sensor 12 in a manner where the test sensor is not turned or rotated 90 degrees. For example, it may be desired to turn the test sensor less than 90 degrees or more than 90 degrees. Furthermore, in an alternative embodiment (not shown), it may be desired to first store the test sensor 12 so that the sides or minor surfaces of the test sensor 12 are parallel to the sidewalls 19,21 and the major surface (or testing surface) is parallel to the top and bottom portions 116,118. This wall cause the test sensor to be rotated onto its side when ejected from the test sensor containing region 16.

As shown in FIG. 5B (and FIGS. 1-2), the test sensor containing region 16 has a tapered shape. The guiding mechanism 150 has a width W1 that is greater than the width W2 of the rear portion 22 of the test sensor containing region 16 wherein the test sensor 12 is stored. In this embodiment, the sidewalls 19,21 that extend between the top portion 116 and bottom portion 118 of the test sensor containing region 16 are tapered in the region between the guide member 154 and rear portion 22. The overall tapered shape of the test sensor containing region 116 lends itself to the cartridges 14a,14b having a semi-circular shape. In other embodiments, the test strip containing region 16 may not include a taper and instead have a continuous width throughout. A test strip containing region 16 may be more desirable in embodiments where the cartridges are not semi-circular.

Figure 6:
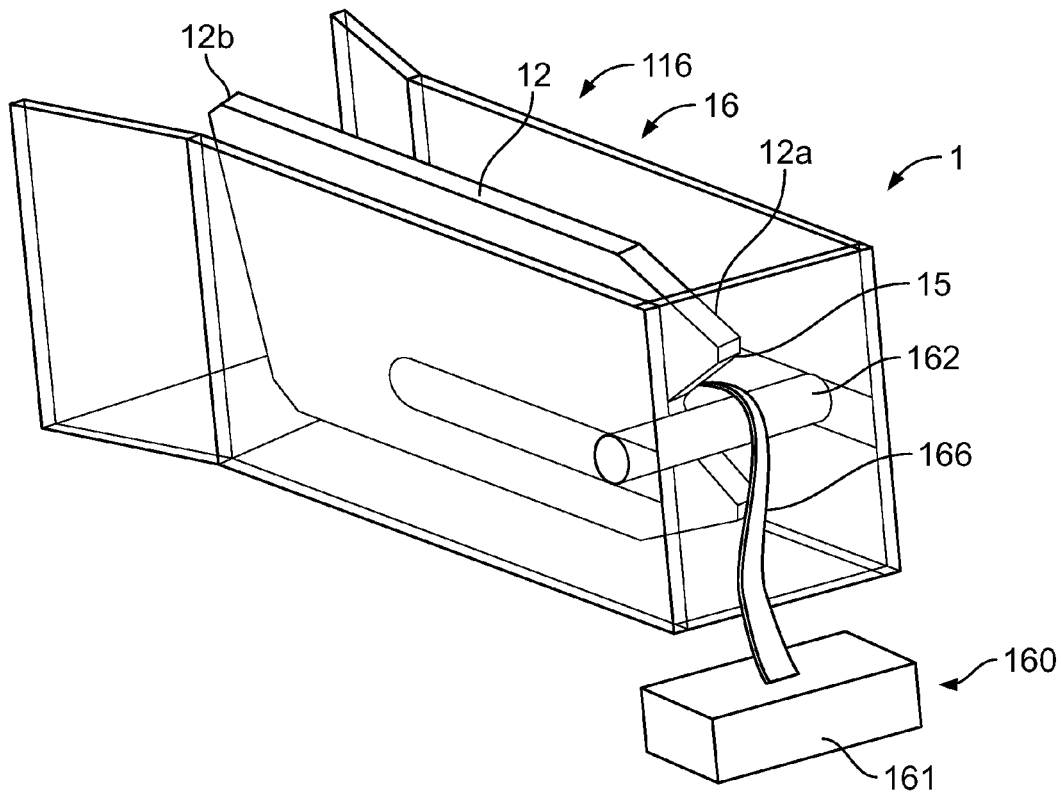
FIG. 6 is a perspective view of a knife assembly engaging a test sensor positioned within a containing region of the packaging assembly of FIG. 1.

With reference to FIG. 6, test sensor packaging assembly 110 includes one or more excision knife assemblies 160 for ejecting test sensors 12 from the test sensor containing regions 16. Each test sensor 12 includes an ejection member or rod 162 configured to engage the excision knife assembly 160. Rod 162 is attached to the first end 12a of test sensor 12. In some embodiments, the first end 12a of test sensor 12 includes a notch or undulation 15 configured and dimensioned for securely receiving the ejection rod 162. Knife assembly 160 includes a base 161 and a knife or blade 166 protruding from the base 161. Knife 166 is adapted to cut foil cover 124 and push (or pull) test sensor 12 as the base 161 is moved along a test sensor containing region 16. Ejection rod 162 is adapted to move along with knife assembly 160. Although FIG. 6 shows knife 166 extending into the test sensor containing region 16 from the bottom portion 118 of the test sensor packaging assembly 110, knife 166 may alternatively extend into the test sensor containing region 16 from rear or top portion 116 of the test sensor packaging assembly 110. As discussed in detail below, test sensor 12 can be ejected from test sensor containing region 16 upon movement of knife assembly 160.

Figure 7:
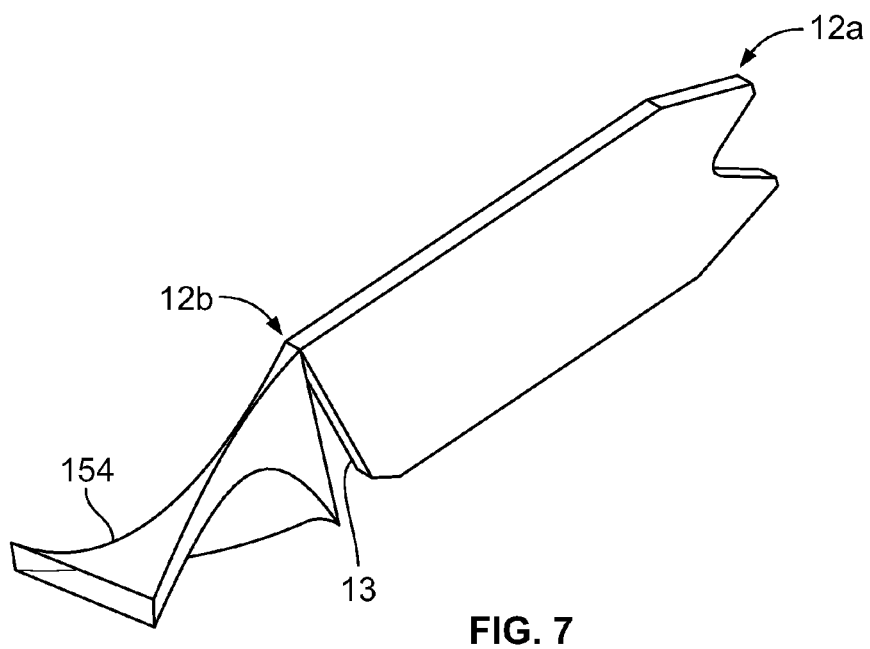
FIG. 7 is a perspective view of a guide member attached to a test sensor according to one embodiment of the present disclosure.
Figure 8:
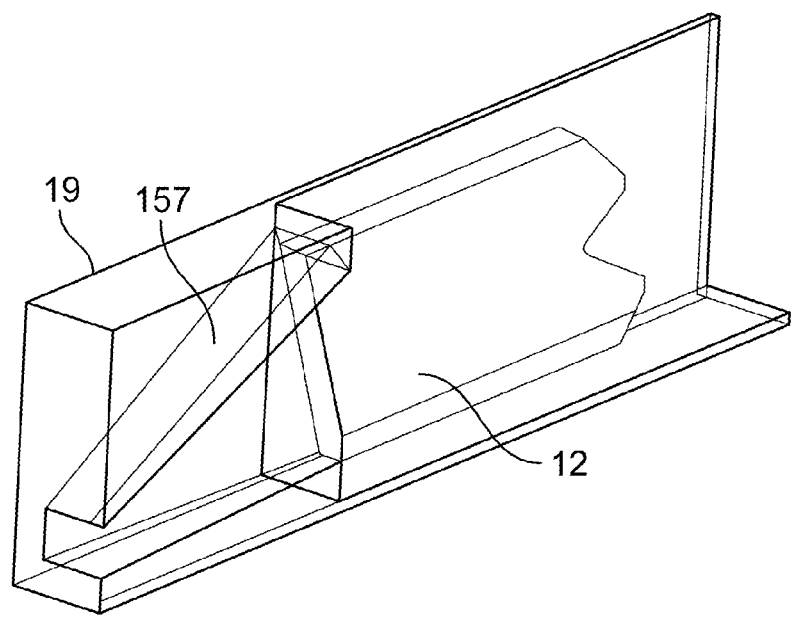
FIG. 8 is a cross-sectional perspective view of the guide member of FIG. 7 attached to the test sensor.
Figure 9:
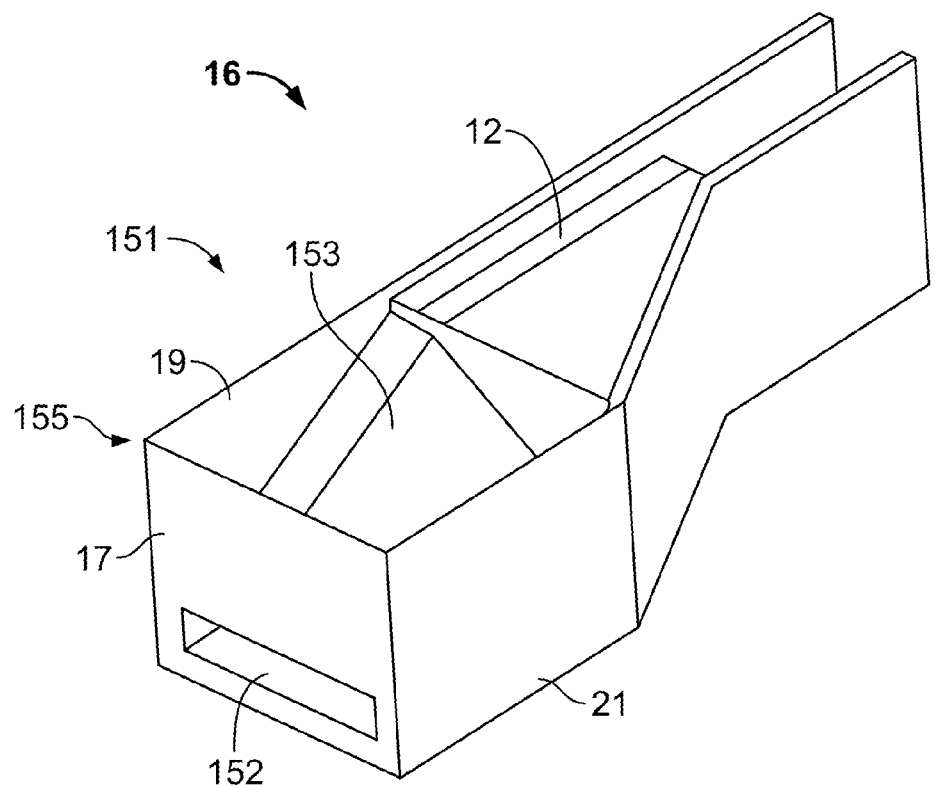
FIG. 9 is an enlarged cut-out perspective view of a single test sensor container region with the guide member of FIG. 8.
Figure 10:
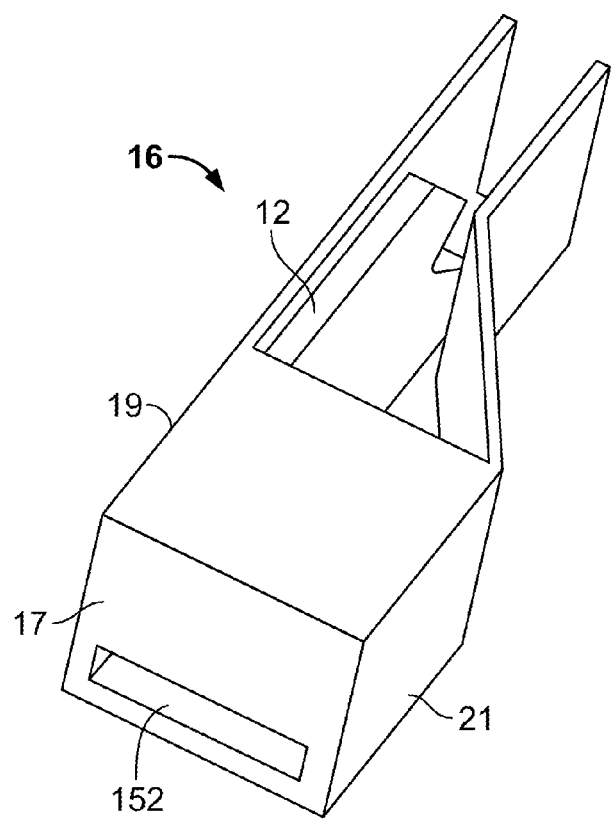
FIG. 10 is an enlarged perspective view of the test sensor containing region of FIG. 9.

As seen in FIG. 7, the second end 12b of test sensor 12 may have an angled face 13 relative to the test sensor sides. In some embodiments, however, the second end 12b of test sensor 12 has a straight face parallel to the test sensor sides. Regardless, a guide member 154 is attached to the second end 12b of test sensor 12. Alternatively, guide member 154 may be monolithically formed with test sensor 12. In the embodiment depicted in FIG. 7, guide member 154 has a partial spiral shape that orients test sensor 12 along a plane substantially parallel to the top portion 116 of test sensor packaging assembly 110 upon ejection. During ejection, as guide member 154 passes through slot 152, test sensor 154 is turned about 90 degrees.

Figure 11:
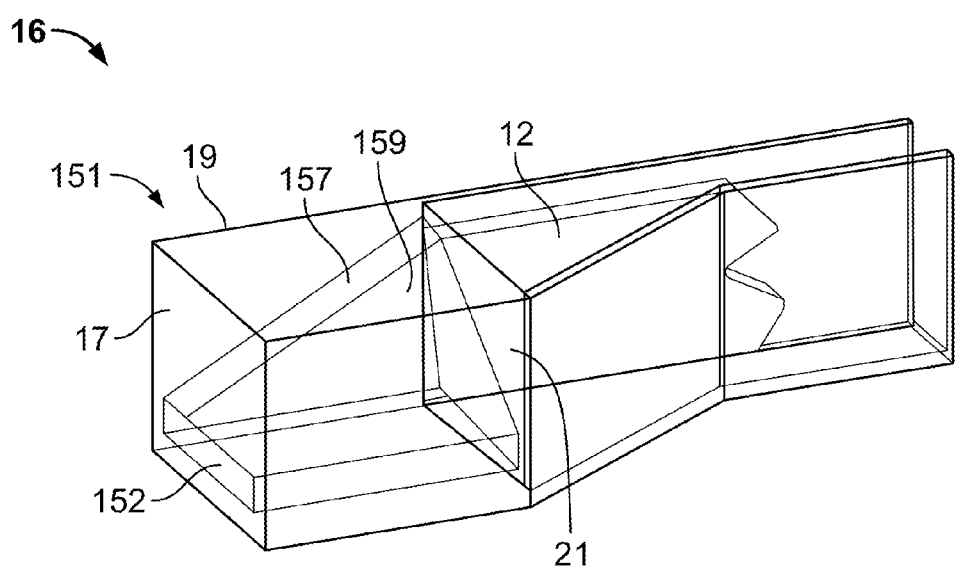
FIG. 11 is an enlarged cross-sectional view of the test sensor containing region with the guide member of FIG. 8.

With reference to FIGS. 8-11, a test sensor containing region 16 includes a guiding mechanism 151 therein for turning the test sensor 12 about 90 degrees during ejection. Guiding mechanism 151 includes a hollow compartment 153 located in an outer region 155 of the test sensor containing region 16. The outer region 155 of the test sensor containing region 16 includes outer wall 17, and two opposite sidewalls 19 and 21. The guiding compartment 153 is configured and dimensioned to receive the test sensor 12 and has a first inclined wall 157 and a second inclined wall 159 (FIG. 11). The first and second inclined walls 157, 159 collectively define a cavity leading to slot 152. The first inclined wall 157 is adjacent to the sidewall 19 of the outer region 155 and extends downwardly along the sidewall at an acute angle in relation to the outer wall 17. In some embodiments, the first inclined wall 157 may be in contact with an inner surface of the sidewall 19. The second inclined wall 159 extends from the first inclined wall 157 to the sidewall 21 of the outer region 155 at an acute angle relative to the sidewall 21. In some embodiments, the second inclined wall 159 may be in contact with the sidewall 21 of the outer region 155.

During ejection, the test sensor 12 is pushed toward the cavity of the hollow compartment 153. Upon entering the hollow compartment 153, the top portions of the test sensor 12 engages the first wall 157. As the test sensor moves towards the slot 152, the first wall 157 urges the top portion of the test sensor 12 downwardly. As a consequence, the bottom portion of the test sensor is urged toward the sidewall 21. At this point, the test sensor 12 begins to turn relative to the slot 152. As the test sensor 12 continues to move toward the slot 152, the test sensors 12 keeps turning until it turns about 90 degrees and can pass through the slot 152 of the test sensor containing region 16.

Figure 12A:
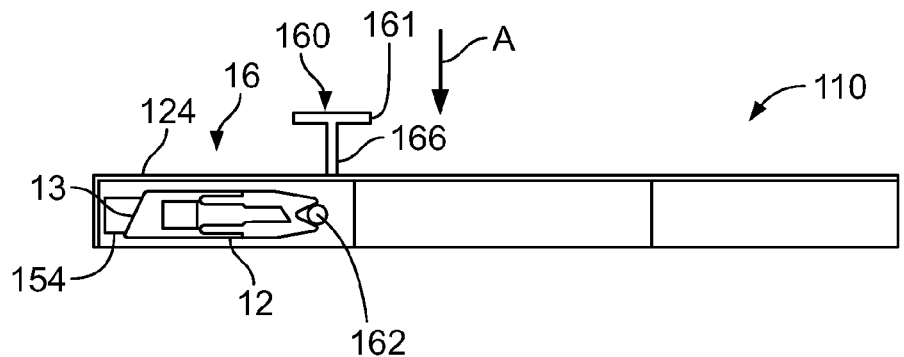
FIGS. 12A-12C show a partial cross-sectional view of the test sensor being dispensed from the sensor packaging assembly of FIG. 1.
Figure 12B:
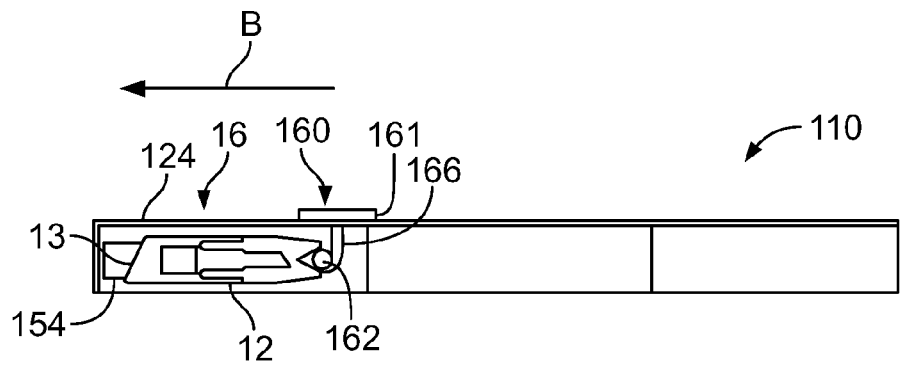
Figure 12C:
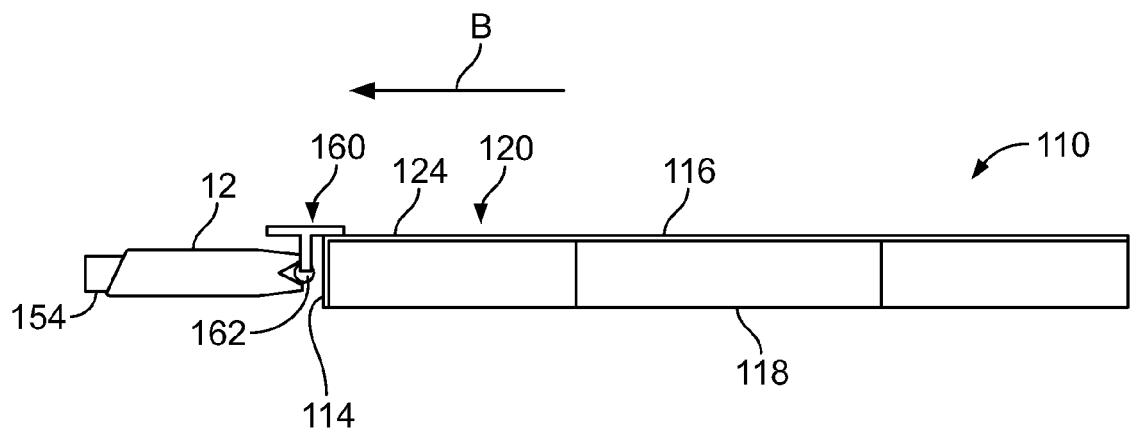

FIGS. 12A-12C illustrate the process of dispensing one test sensor 12 from among the plurality of test sensors 12 stored in a housing segment 14a or 14b. In one exemplary method, knife assembly 160 is positioned above foil cover 124 over one of the test sensor containing regions 16. Then, knife assembly 160 is moved in the direction indicated by arrow A to puncture foil cover 124 with blade 166. As depicted in FIG. 12B, blade 166 of knife assembly 160 engages the ejection rod 162 after the blade 166 has pierced foil cover 124. As shown in FIG. 12C, knife assembly 160 is then moved in the direction indicated by arrow B (i.e., a radially outward direction) to eject test sensor 12 out of the test sensor containing region 16. As knife assembly 160 moves, blade 166 cuts the portion of the foil cover 124 sealing the top portion 116 of test sensor packaging assembly 110, especially the portion of the foil cover 124 sealing the test sensor containing region 16 containing the test sensor 12 being ejected. The movement of knife assembly 160 also urges test sensor 12 toward the outer periphery 114 of test sensor packaging assembly 110. The guide member 154 and/or the test sensor 12 eventually contacts and pierces the portion of the foil cover 124 covering the outer periphery 114 of the test sensor packaging assembly 110. Before puncturing the portion of the foil cover 124 sealing the outer periphery 114 of the test sensor packaging assembly 110, at least a leading portion of guide member 154 passes through slot 152 of the test sensor containing region 16. As test sensor 12 moves radially outward, guide member 154 engages slot 152 of test sensor containing region 16, causing the test sensor 12 to turn about 90 degrees. At the end of the ejection process, test sensor 12 is oriented substantially parallel to the top and/or bottom portions 116, 118 of the test sensor packaging assembly 110, as shown in FIG. 12C. At this point, any suitable fluid sample may be applied to the ejected test sensor 12. Test sensor 12 then determines, for example, the glucose concentration level on such fluid sample. Specifically, the reagent contained in the test sensor 12 produces a measurable reaction with an analyte (e.g., glucose) indicative of the presence and/or concentration of such analyte in the fluid sample. Any suitable analyte measuring device then displays the analyte reading to the user. Alternatively, the test sensor 12 may be removed for use with a separate meter.

In the exemplary process depicted in FIGS. 12A-12C, blade 166 of knife assembly 160 only cuts the portion of foil cover 124 sealing only one test sensor containing region 16 during the ejection. Other portions of foil cover 124 remain intact and continue to seal the other test sensor containing regions 16. Accordingly, the ejection of a single test sensor 12 does not break the seal over the other test sensors 12. On the contrary, during the ejection process, only one test sensor containing region 16 is opened, while the other test sensor containing region 16 remains sealed. Thus, while a test sensor 12 is being ejected, the foil cover 124 seals and protects the remaining test sensors 12. Consequently, there is no need to open and close the test sensor containing regions 16 multiple times.

The user must use a different test sensor 12 for every test. Once all or some of the test sensors 12 stored in the test sensor packaging assembly 110 have been used, the user may replenish the analyte measuring system by replacing only one of the housing segments 14a, 14b. The user can also replace all the housing segments 14a, 14b. Though the preferred embodiment of the test sensor packaging assembly 110 includes two housing segments 14a, 14b, the test sensor packaging assembly 110 may include many more segments, up to a practical limit. For example, test sensor packaging assembly 110 may include five (5) housing segments.

The following numbered paragraphs describe features in accordance with some embodiments of the disclosure:

1. A packaging container for holding a plurality of test sensors, comprising:
a first semi-circular housing having a plurality of first test sensor containing regions, each of the plurality of the first test sensor containing regions being adapted to contain at least one test sensor; and
a second semi-circular housing having a plurality of second test sensor containing regions, each of the plurality of the second test sensor containing regions being adapted to contain at least one test sensor,
the second semi-circular housing having a top portion, the first semi-circular housing and the second semi-circular housing being positioned adjacent to each other.

2. The packaging container of paragraph 1, wherein said first semi-circular housing further comprises an outer wall extending in a non-perpendicular manner from said top portion.

3. The packaging container of paragraph 1, wherein said first semi-circular housing may be removed from said packaging container and replaced with a third semi-circular housing having a plurality of third test sensor containing regions, each of the plurality of the third test sensor containing regions being adapted to contain at least one test sensor.

4. The packaging container of paragraph 3, wherein the first semi-circular housing may be replaced with the third semi-circular housing while the second semi-circular housing is still in place.

5. The packaging container of paragraph 1, wherein breaking the foil cover only opens individual test sensor containing regions of the plurality of the test sensor containing regions.

6. The packaging container of paragraph 1, wherein said first semi-circular housing and said second semicircular housing combine to form a circular cartridge.

7. A packaging container for holding a plurality of test sensors, comprising:
at least two housings forming at least a portion of a circle, each housing having at least one test sensor containing region, the test sensor containing regions being adapted to contain at least one test sensor, the housings having top portions and bottom portions that are substantially parallel with respect to each other, each top portion being covered by a foil cover; and a guiding system for guiding the ejection of each test sensor from each test sensor containing region, the guiding system including a guide member associated with each test sensor and a slot defined along an outer wall of each test sensor containing region, the slot being dimensioned to receive the guide member and the test sensor, the guide member having a shape that allows the test sensor to turn about 90 degrees when ejected from the test sensor containing region.

8. The packaging container of paragraph 7, wherein the guide member has a partial spiral shape.

9. The packaging container of paragraph 7, wherein the at least two housings is only two housings.

10. The packaging container of paragraph 7, wherein the outer wall is tapered with respect to the top portions and bottom portions of said housing.

11. The packaging container of paragraph 7, wherein the guiding system is adapted to cut the foil cover.

12. A method for replacing a housing of a packaging container, comprising:
providing a packaging container including at least two housings forming at least a portion of a circle, each housing having at least one test sensor containing region, the test sensor containing regions being adapted to contain at least one test sensor;
replacing one housing of the at least two housings with another housing while the remaining housings remain in the packaging container.

13. A packaging container for holding a plurality of test sensors, comprising:
at least two housings forming a circle, each housing having at least one test sensor containing region covered by a foil cover, each test sensor containing region being adapted to contain at least one test sensor and having a guiding mechanism for turning the at least one test sensor about 90 degrees upon ejection from one of the at least two housings, the guiding mechanism including:
a hollow compartment in an outer region of each test sensor containing region, the hollow compartment including a first inclined wall and a second inclined wall, the first inclined wall being oriented at an acute angle relative to the second inclined wall so that the at least one test sensor turns about 90 degrees upon passing through the hollow compartment.

It will be appreciated that various features set forth in the embodiments discussed herein can be combined in different ways then presented herein. It will also be appreciated that the features described in connection with individual embodiments may be shared with other embodiments discussed herein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as detailed by the following claims.

The invention claimed is:

1. A packaging container for holding a plurality of test sensors, comprising:
at least two housings forming at least a portion of a circle, each of the at least two housings having at least one test sensor containing region, the test sensor containing regions being adapted to contain at least one test sensor, the housings having top portions and bottom portions that are substantially parallel with respect to each other, each top portion being covered by a foil cover; and
a guiding system for guiding the ejection of each test sensor from each test sensor containing region, the guiding system including a guide member associated with each test sensor and a slot defined along an outer wall of each test sensor containing region, the slot being dimensioned to receive the guide member and the test sensor, the guide member having a shape that allows the test sensor to rotate from a first position to a second position when ejected from the test sensor containing region.

2. The packaging container of claim 1, wherein the test sensor rotates about 90 degrees when moving from the first position to the second position.

3. The packaging container of claim 1, wherein the at least two housings further comprise opposed sidewalls extending between the top and bottom portions, wherein when the at least one test sensor in each of the two housings is in the first position, each of the at least one test sensors has a major surface parallel to the opposed sidewalls and a minor surfaces parallel to the top portion, and wherein when the test sensor is in the second position, the major surface of the test sensor is parallel to the top portion and the minor surface is parallel to the opposed sidewalls.

4. The packaging container of claim 1, wherein the housings further comprise opposed sidewalls extending between the top and bottom surfaces, wherein when the test sensor is in the first position, the test sensor has a minor surface parallel to the opposed side walls and major surfaces parallel to the top surface, and wherein when the test sensor is in the second position, the minor surface of the test sensor is parallel to the top surface and the major surface is parallel to the sidewalls.

5. The packaging container of claim 1, wherein the guide member has a partial spiral shape.

6. The packaging container of claim 1, wherein the at least two housings is only two housings.

7. The packaging container of claim 1, wherein the outer wall is tapered with respect to the top portions and bottom portions of said housing.

8. The packaging container of claim 1, wherein the guiding system is adapted to cut the foil cover.

9. The packaging container of claim 1 further comprising a cutting assembly for cutting the foil cover, the cutting assembly comprising a base and a cutting edge extending from the base, wherein movement of the base causes movement of the cutting edge across the foil cover.

10. A packaging container for holding a plurality of test sensors, comprising:
at least two housings forming a circle, each housing having at least one test sensor containing region covered by a foil cover, each test sensor containing region being adapted to contain at least one test sensor and having a guiding mechanism for turning the at least one test sensor about 90 degrees upon ejection from one of the at least two housings, the guiding mechanism including:
a hollow compartment in an outer region of each test sensor containing region, the hollow compartment including a first inclined wall and a second inclined wall, the first inclined wall being oriented at an acute angle relative to the second inclined wall so that the at least one test sensor turns about 90 degrees upon passing through the hollow compartment.

11. The packaging container of claim 10, wherein the hollow compartment further comprises a slot dimensioned to receive the test sensor, the slot being positioned on an outer surface of the test sensor containing region.

12. The packaging container of claim 11, wherein the guiding mechanism further comprises a guide member configured to guide the test sensor through the slot.

13. The packaging container of claim 12, wherein the guide member is dimensioned to slidably pass through the slot.

14. The packaging container of claim 12, wherein the guide member has a partial spiral shape.

15. The packaging container of claim 10, wherein the at least two housings is only two housings.

16. The packaging container of claim 10, wherein the at least two housings includes more than two housings.

17. The packaging container of claim 10, further comprising a cutting assembly for cutting the foil cover, the cutting assembly comprising a base and a cutting edge extending from the base, wherein movement of the base causes movement of the cutting edge across the foil cover.

* * * * *

UNITED STATES PATENT AND TRADEMARK OFFICE
CERTIFICATE OF CORRECTION

| | | |
|---|---|---|
| PATENT NO. | : 9,097,700 B2 | Page 1 of 1 |
| APPLICATION NO. | : 13/729765 | |
| DATED | : August 4, 2015 | |
| INVENTOR(S) | : Daniel Brown, Martin Antoine Mathelier and Sung-Kwon Jung | |

It is certified that error appears in the above-identified patent and that said Letters Patent is hereby corrected as shown below:

IN THE SPECIFICATION

In Column 2, Line 46, delete "about degrees" and insert -- about 90 degrees --, therefor.

In Column 8, Line 18, delete "region 116" and insert -- region 16 --, therefor.

In Column 8, Line 57, delete "sensor 154" and insert -- sensor 12 --, therefor.

IN THE CLAIMS

In Column 12, Line 18, in Claim 3, delete "a minor surfaces" and insert -- a minor surface --, therefor.

In Column 12, Line 27, in Claim 4, delete "and major surfaces" and insert -- and a major surface --, therefor.

Signed and Sealed this
Fifteenth Day of March, 2016

Michelle K. Lee
*Director of the United States Patent and Trademark Office*